(12) United States Patent
Porreca et al.

(10) Patent No.: US 10,061,953 B2
(45) Date of Patent: Aug. 28, 2018

(54) DEVICES AND SYSTEMS FOR BARCODING INDIVIDUAL WELLS AND VESSELS

(71) Applicant: Good Start Genetics, Inc., Cambridge, MA (US)

(72) Inventors: Gregory Porreca, Cambridge, MA (US); Mark Umbarger, Brookline, MA (US); Athurva Gore, Cambridge, MA (US)

(73) Assignee: Good Start Genetics, Inc., Cambridge, MA (US)

( * ) Notice: Subject to any disclaimer, the term of this patent is extended or adjusted under 35 U.S.C. 154(b) by 44 days.

(21) Appl. No.: 14/994,325

(22) Filed: Jan. 13, 2016

(65) Prior Publication Data

US 2016/0210486 A1    Jul. 21, 2016

Related U.S. Application Data

(60) Provisional application No. 62/103,716, filed on Jan. 15, 2015.

(51) Int. Cl.
| | |
|---|---|
| *G06K 9/46* | (2006.01) |
| *G06K 9/66* | (2006.01) |
| *G06K 7/10* | (2006.01) |
| *G06K 9/62* | (2006.01) |
| *G06K 19/06* | (2006.01) |
| *G01N 35/00* | (2006.01) |
| *B01L 3/00* | (2006.01) |
| *B01L 9/06* | (2006.01) |

(52) U.S. Cl.
CPC ........ *G06K 7/10554* (2013.01); *B01L 3/5453* (2013.01); *G01N 35/00732* (2013.01); *G06K 9/6217* (2013.01); *G06K 19/0614* (2013.01); *G06K 19/06028* (2013.01); *G06K 19/06037* (2013.01); *B01L 3/5021* (2013.01); *B01L 3/50855* (2013.01); *B01L 9/06* (2013.01); *B01L 2200/025* (2013.01); *B01L 2300/021* (2013.01); *B01L 2300/0829* (2013.01); *G01N 2035/00752* (2013.01)

(58) Field of Classification Search
CPC ............ G06K 7/10554; G06K 9/6217; G06K 19/060208; B01L 3/5453; G01N 35/00732

See application file for complete search history.

(56) References Cited

U.S. PATENT DOCUMENTS

| | | |
|---|---|---|
| 5,060,980 A | 10/1991 | Johnson et al. |
| 5,459,307 A | 10/1995 | Klotz, Jr. |
| 5,486,686 A | 1/1996 | Zdybel, Jr. et al. |
| 7,774,962 B1 * | 8/2010 | Ladd ................. G09F 3/0295 215/286 |

(Continued)

OTHER PUBLICATIONS

U.S. Appl. No. 29/518,525, filed Feb. 24, 2015, including amended figures.

*Primary Examiner* — Gregory M Desire
(74) *Attorney, Agent, or Firm* — Brown Rudnick LLP; Thomas C. Meyers

(57) ABSTRACT

The invention generally relates to devices and systems for individually barcoding sample vessels. In certain embodiments, the devices comprise an attachment member and an extension member, where the extension member can accommodate an identifier, such as a barcode. When loaded into a substrate, the barcoded vials are scanned by a barcode reader.

43 Claims, 13 Drawing Sheets

(56) References Cited

U.S. PATENT DOCUMENTS

| | | | |
|---|---|---|---|
| 8,474,228 B2* | 7/2013 | Adair | B01L 9/06 |
| | | | 53/158 |
| 8,496,166 B2* | 7/2013 | Burns | G06K 5/02 |
| | | | 235/375 |
| 2003/0078496 A1* | 4/2003 | Price | G06F 11/023 |
| | | | 600/431 |
| 2014/0318274 A1* | 10/2014 | Zimmerman | G01N 30/24 |
| | | | 73/863 |
| 2014/0361022 A1* | 12/2014 | Finneran | B01L 9/06 |
| | | | 220/628 |
| 2016/0210486 A1* | 7/2016 | Porreca | G06K 7/10554 |

* cited by examiner

DEVICES AND SYSTEMS FOR BARCODING INDIVIDUAL WELLS AND VESSELS

CROSS-REFERENCE TO RELATED APPLICATIONS

This application claims priority to U.S. Provisional Application No. 62/103,716, filed on Jan. 15, 2015, the contents of which are incorporated by reference.

FIELD OF THE INVENTION

The present invention relates to devices and systems for attaching a barcode to an individual well or sample vessel.

BACKGROUND

Barcodes are essential in automated laboratories to track samples and to direct well plates to the next step in the workflow. As automated laboratory instruments move barcoded plates from instrument to instrument, the well plate's barcode is scanned and uploaded into the laboratory's computer system. This computer system can locate and track barcoded plates at any time.

Although well plates are barcoded, individual wells or small sample vessels are unable to accommodate a barcode. This results in individual wells or sample vessels not being individually tracked during a laboratory process. Although a barcode can be applied to the side of a sample vessel, the label's location requires manual scanning, making it incompatible with automated processes.

SUMMARY

The devices of the present invention attach a barcode directly to a vessel, where the barcode is compatible with automated laboratory processes. Also, access to the vessel's interior is not restricted. As a result, laboratories can integrate individual test tubes and sample wells within the workflow of automated laboratory processes.

The device in the present invention can be attached to a sample vessel. For example, in some embodiments, the device has a collar to fit around the shaft of a test tube. The device can be formed in any size or configuration, making it compatible with test tubes of varying sizes. Also, the device does not interfere with the loading and unloading of samples and reagents. Additionally, the collar of the device may include recesses or key holes to fit a portion of the sample vessel, such as test tube cap or other protrusions/features. These recesses secure the collar to the shaft of the test tube, preventing the test tube from rotating within the collar.

The device also has a platform to accommodate a label, such as a barcode. A barcode or any other identifying mark can be affixed to this surface. Importantly, the platform orients the barcode, so the barcode can be scanned during automated laboratory processes. Additionally, the platform and identifying mark are configured to allow access to the interior of the sample vessel while displaying the identifying mark. This platform may also have a protrusion. The protrusion can be shaped to fit within a well of a well plate or a recess in a substrate. In some aspects, several sample vessels with an attached barcode can be placed within a substrate. This feature of the invention allows several individual barcodes to be scanned simultaneously, even during automated processes. The scanned barcodes are uploaded and stored within a computer database or a computer system.

DETAILED DESCRIPTION

Figure 1:
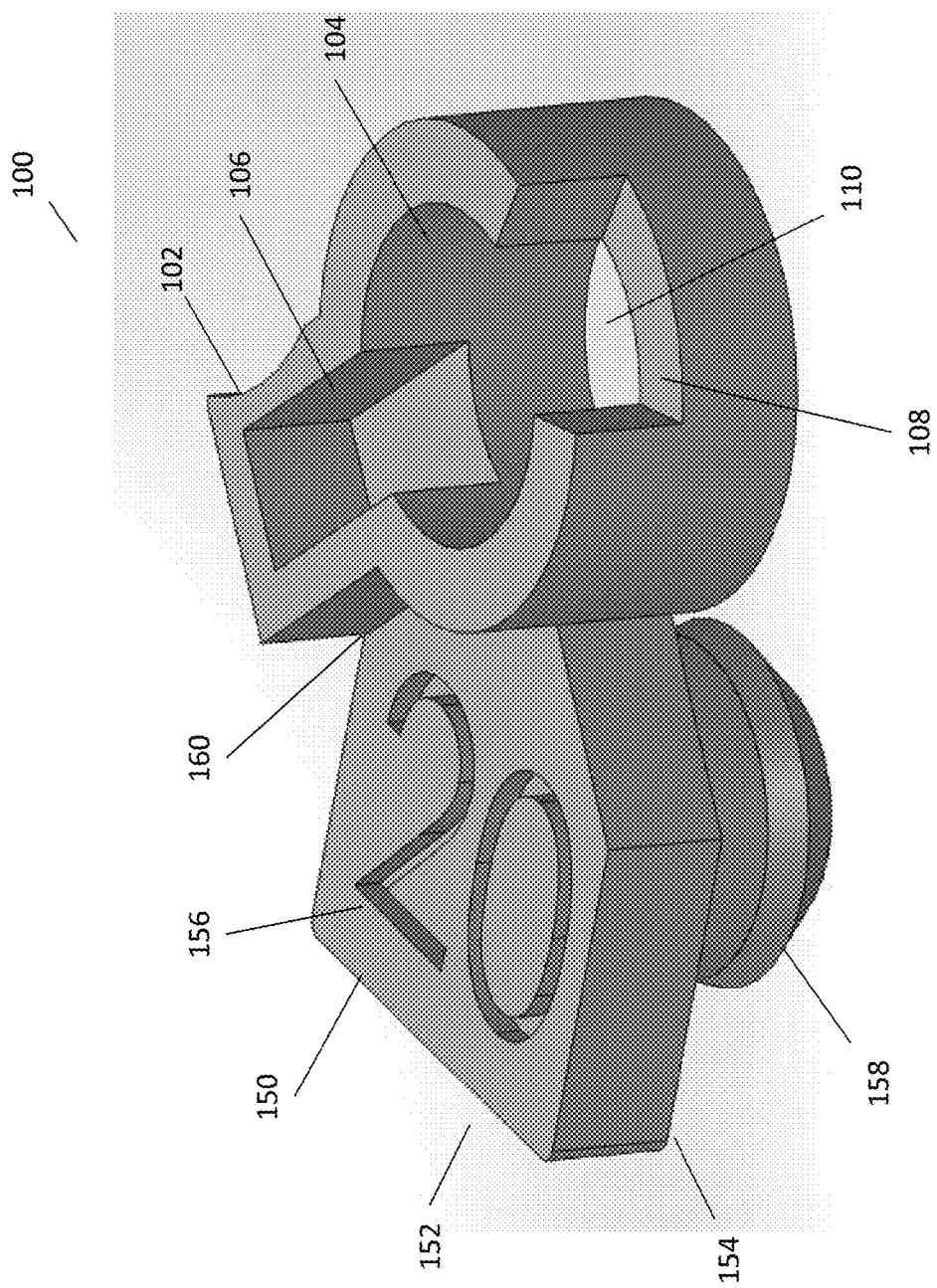
FIG. 1 depicts an embodiment of a device of the present invention.

The invention provides devices and systems for associating a barcode with a vessel such as a test tube or well. Specifically, the devices of the present invention associate a specific barcode with a particular sample vessel. The systems of the present invention allow for a plurality of barcoded sample vials to be placed within a substrate, such as standardized plate. Once placed within a substrate, the device's configuration positions the barcodes for scanning by a barcode scanner.

The devices of the present invention generally comprise an attachment member and an extension member. The attachment member is joined to the extension member. The attachment member attaches to or receives a sample vessel. The devices of the present invention can be manufactured or constructed to attach to or receive various sizes of sample vessels. Sample vessels can include test tubes, vials, centrifuge tubes, microcentrifuge tubes, polymerase chain reaction tubes, culture tubes, screw cap tubes, or similar laboratory containers. The extension member extends from the attachment member and has an exposed surface area. The surface area of the extension member accommodates one or more identification marks.

Additionally, the extension member can have varied positions with respect to the attachment member. The extension member and the attachment member can be adjacent and parallel to each other, or lie in the same plane. Alternatively, the extension member can be positioned at a slight angle with respect to the attachment member. In other words, the extension member can be positioned to angle upwards or downwards, or slightly bent upwards or downwards. The extension member can be positioned at any angle, upwards or downwards, from 0 to 90°. Similarly, the extension member can be positioned perpendicular to the attachment member. Additionally, the extension member can be positioned to lie next to or adjacent to the attachment member. In this manner, the attachment member is able to receive a vessel and a user can access the vessel without interference from the extension member. In other words, the extension member does not block or obscure the vessel opening.

The device can be separate from the vessel and attachable to the vessel, as described herein. Alternatively, the vessel and the device can be formed integrally as a single unit.

A variety of materials and methods can be used to form any of the described components of the systems and devices of the invention. For example, various components of the invention can be formed from solid materials and can be formed via molding, micromachining, film deposition processes, laser fabrication, photolithographic techniques, stereolithography, additive manufacturing or three dimensional printing, etching methods including wet chemical or plasma processes, and the like. Various components of the systems and devices of the invention can also be formed of a polymer, such as an elastomeric polymer like polydimethylsiloxane ("PDMS"), polytetrafluoroethylene ("PTFE") or Teflon®. Different components can be formed of different materials. For example, a portion such as the attachment member can be formed from an opaque material (silicone or PDMS), and the extension member can be formed from a transparent or at least partially transparent material (glass or a transparent polymer).

Various components of the invention, when formed from polymeric and/or flexible and/or elastomeric materials, can be conveniently formed of a hardenable fluid, facilitating formation via molding (e.g. replica molding, injection molding, cast molding, etc.). The hardenable fluid can be essentially any fluid that can be induced to solidify, or that spontaneously solidifies, into a solid. The hardenable fluid may comprise a polymeric liquid or a liquid polymeric precursor (i.e. a "prepolymer"). Examples of suitable polymeric liquids include thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent by evaporation or otherwise. Such polymeric materials, which can be solidified from a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers can be used in forming the components of the devices, such as, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties that simplify formation of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

In a particular embodiment, a portion of the device is formed of a material different from another portion or other component. Components can be sealed together with adhesives. Where it is desired to seal a component comprising a silicone polymer (e.g. PDMS) to a different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

The attachment member of the device attaches, surrounds, affixes, contacts, or engages a sample vessel. In a preferred embodiment, the attachment member is a collar that fits on the shaft of a sample vessel. In this embodiment, a sample vessel is placed and inserted within the collar to form a tight fit between the collar and the sample vessel. In preferred embodiments, the collar is in direct frictional contact with the shaft of the vessel, holding the collar to the vessel against the forces of gravity.

In some embodiments, the attachment member is permanently affixed to a sample vessel. In these embodiments the attachment member is bound to the sample vessel by glue, epoxy, cement, mucilage, paste, or other adhesives that resists separation. Additionally, the attachment member may be bound to the sample vessel by thermal bonding, chemical bonding, welding, or soldering.

In preferred embodiments of the device, the attachment member has recesses to fit various components of the sample vessel to provide a secure fit. Recesses can also be configured to accommodate protrusions or features of a sample vessel. For example, the attachment member can contain a recess to receive a portion of a sample vessel. When the sample vessel is inserted into the attachment member, a portion of the sample vessel nestles in the recess. This prevents rotation of the sample vessel within the attachment member. However, the sample vessel can be removed from the attachment vessel.

A preferred embodiment of the invention is depicted in FIG. 1. FIG. 1 depicts device 100 which comprises an attachment member 104 and an extension member 150. The attachment member 104 as shown in FIG. 1 is a collar 104 with a generally cylindrical shape. Attachment member 104 has recesses 106 and 108. The attachment member 104 is connected to extension member 150 at 160. In some embodiments, the attachment member and the extension member are formed within the same mold to provide a single unit comprising the two parts. In other embodiments, the attachment member and the extension member are manufactured separately and sealed or joined together. Extension member 150 has a top portion 152 and a bottom portion 154. The top portion 152 accommodates an identifying mark 156, which is shown as a number. It should be appreciated that the identifying mark can be a barcode, a number(s), a letter(s), a symbol(s), or alphanumeric character(s). It should be appreciated that the device of the present invention allows for the displaying of the identifying mark(s) while allowing access to the interior of the vessel. This feature makes the device compatible for automated laboratory processes. In some embodiment of the invention, the extension member is juxtaposed to the attachment member and the vessel opening. In this embodiment the identifying mark is displayed and the opening to the vessel is unobscured. In this aspect, the identifying mark is displayed for detection by a barcode scanner, and the vessel opening is accessible simultaneously.

The bottom portion 154 of the extension member 150 has a protrusion 158. The protrusion 158 can be configured to any shape or size. The shape and size of the protrusion depends upon the configuration of a substrate. It should be appreciated that the substrates can be customized, or the substrates could be common and standardized within an industry. For example, well plate standards are governed by the ANSI/SLAS standards. The standards governs various characteristics including well dimensions (e.g. diameter, spacing and depth) as well as plate properties (e.g. dimensions and rigidity) (typical dimension ~5"×3.33"), which allows interoperability between plates, instrumentation and equipment from different suppliers, and is particularly important in laboratory automation. In some embodiments, protrusion 158 is configured to fit within a well in a standardized well plate.

Device 100 is able to receive a sample vessel, such as a test tube or reaction vessel through the opening 110. The attachment member 104 contacts the shaft of the vessel. In some embodiments the attachment member fits snugly around the shaft of the vessel providing a tight fit.

Although FIG. 1 depicts a device with an attachment member configured as a collar, other configurations for the attachment member can be used. In some embodiments, the attachment member comprises a first arm and a second arm, where the arms are configured to open and close around a sample vessel, securing the device to the vessel. The first and second arms may be held together by a pin, spring, or similar connector. In another embodiment, the attachment member can comprise a single arm, where the arm moves from a first position to open and wrap around the vessel. It should be appreciated that similar clamping or frictional forces can be employed to secure the device to a sample vessel.

Figure 2:
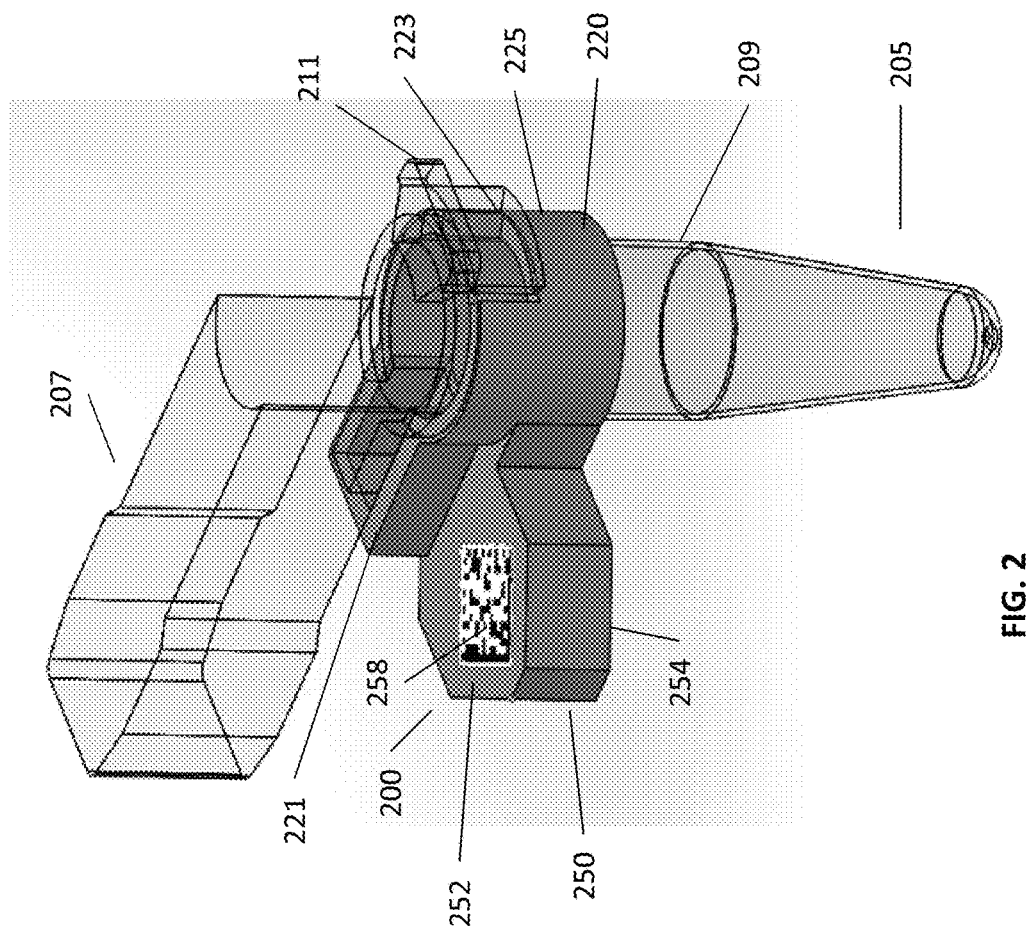
FIG. 2 depicts an embodiment of a device of the present invention.

FIG. 2 depicts another embodiment of the device of the invention. FIG. 2 depicts device 200 which is shown coupled to vessel 205. Vessel 205 comprises a cap 207, a shaft 209 and a protrusion 211. Device 200 has an attachment member 250 which has a top portion 252 and a bottom portion 254. The top portion 252 has an identifying mark 258. It should be appreciated that in some embodiments, the bottom portion 254 may accommodate an identifying mark. In these embodiments, the identified mark may be detected from underneath the device. In other embodiments, the device is constructed from a translucent or transparent material, where the identifying mark on the bottom portion 254 is detected from above the device, or detecting through the material of the device. It should be appreciated that the device could be constructed from any translucent or transparent material such as glass, calcite, quartz, poly(methyl methacrylate), polycarbonate, polyethylene, polyethylene terephthalate, Pyrex, or RGD720, a multipurpose transparent PolyJet photopolymer for standard clear plastics. The attachment member 220 is configured as a collar that fits around the shaft 209 of the vessel. The attachment member 220 also comprises a recess 221 that receives a portion of the cap 207. In some embodiments, recess 221 is configured such that device 200 or the attachment member does not interfere with the opening and closing the cap 207. In some embodiments, the device 200 comprises a second recess 223 that is capable of receiving protrusion 211 of vessel 205.

As shown in FIG. 2, the extension member 250 of the device 200 accommodates an identifying mark 258 in a fixed position. In some embodiments, the extension member is held in a fixed and rigid position. In some embodiments, the identifying mark is a barcode. The extension member is configured to position the barcode so that a barcode reader can scan the barcode. In some embodiments, the identifying mark is displayed so that a barcode reader positioned above the device is able to scan the barcode.

It should be appreciated that the devices of the present invention can accommodate any identifying mark. In some embodiments, the identifying mark is a number, a letter, color, or an alphanumeric reference. The identifying mark could be black, white, or any color. For example, the identified mark could be a colored number, a colored letter, or a colored shape. In addition, a feature or area of the device could be colored. The identifying mark can also be a symbol. It should be appreciated that an identifying mark can be any combination of letters, numbers, symbols, barcodes, color, etc. For example, an identifying mark could be a number(s) and a barcode, or a barcode and a letter(s). In preferred embodiments, the identifying mark is a barcode. It should be appreciated that any type of barcode may be used in the present invention. For example, numeric-only barcodes, alpha-numeric barcodes, 2-dimensional barcodes, industrial standard barcodes, colored barcodes, or graphical barcodes. There exist a vast amount of barcode standards, such as Code128, 2 of 5 Interleaved, 2 of 5 Standard, 2 of 5 IATA, Code39, EAN8, EAN13, EAN128/GS1-128, UPCA, Code11, UCC 128, ISBN, QR code, etc., defining how the barcodes look like, their allowed sizes and how they are read and decoded. The most common barcodes are known as one-dimensional barcodes. These graphical patterns vary in a single dimension (e.g. the horizontal dimension), and are constant in the other dimension (e.g., the vertical dimension). One-dimensional barcodes are employed in low information content applications like product index registry (e.g. automatic price tagging and inventory management), or serial number registry. These barcodes typically encode limited information, such as the price of the item and the manufacturer.

Two-dimensional barcodes are able to convey more information in the same surface area. Two-dimensional barcodes involve intricate patterns that vary in both the horizontal and the vertical dimensions. For example, two-dimensional barcodes can be used to encode mail addresses for automated mail reading and distribution systems. In another example, two-dimensional barcodes can be used to encode the compressed content of a printed page to avoid the need for optical character recognition at the receiving end. U.S. Pat. Nos. 5,060,980, 5,486,686, and 5,459,307 illustrate an exemplary 2D barcode system. This system utilizes short black bars that have a forward orientation or a backward orientation (e.g., bars that are oriented at either 45% or 135% with respect to a reference) to render the barcode. The two possible orientations of the bar allow information (e.g., 1 or 0) to be encoded therein.

In preferred embodiments, the extension member members accommodate two-dimensional barcodes. As discussed above, two-dimensional barcodes are able to contain more information in a smaller space.

It is also an aspect of the invention that the devices can be incorporated into a substrate, such as a well plate. When a plurality of the devices are positioned or placed within a standardized substrate, the devices are seamlessly integrated into automated laboratory processes. For example, barcoded sample vessels can be scanned into an automated laboratory system. Laboratory automation is defined as the use of technology to streamline or substitute manual manipulation of equipment and processes. Laboratory automation offers technologies and engineering backing for state-of-the-art work flows in research, quality assurance, and diagnostics labs. Lab automation techniques are broadly finding applications in a majority of lab procedures—from simple capping and decapping of sample bottles to high throughput screening of test samples.

As samples and reagents are added to the barcoded vessels, the automated system updates this information in the laboratory's computer system. As the vessel is moved from instrument to instrument, the position in the laboratory is tracked. It is common in such laboratories that reagents, pipettes, instruments, etc. are barcoded. Whenever a step is attempted or completed, the barcodes are scanned and the database is updated. For example, if reagent A is added to vessel B by pipette C on instrument D, the automated system scans the barcodes of components A, B, C and D and the database is updated. Such a system and associated database may be a Laboratory Information Management System (LIMS), a software-based laboratory and information management system. Key features include workflow and data tracking support, flexible architecture, and laboratory informatics management. LIMS are instrumental in various laboratory functions such as the reception and log in of a sample and its associated customer data; the assignment, scheduling, and tracking of the sample and the associated analytical workload; the processing and quality control associated with the sample and the utilized equipment and inventory; the storage of data associated with the sample analysis; and the inspection, approval, and compilation of the sample data for reporting and/or further analysis.

Figure 3A:
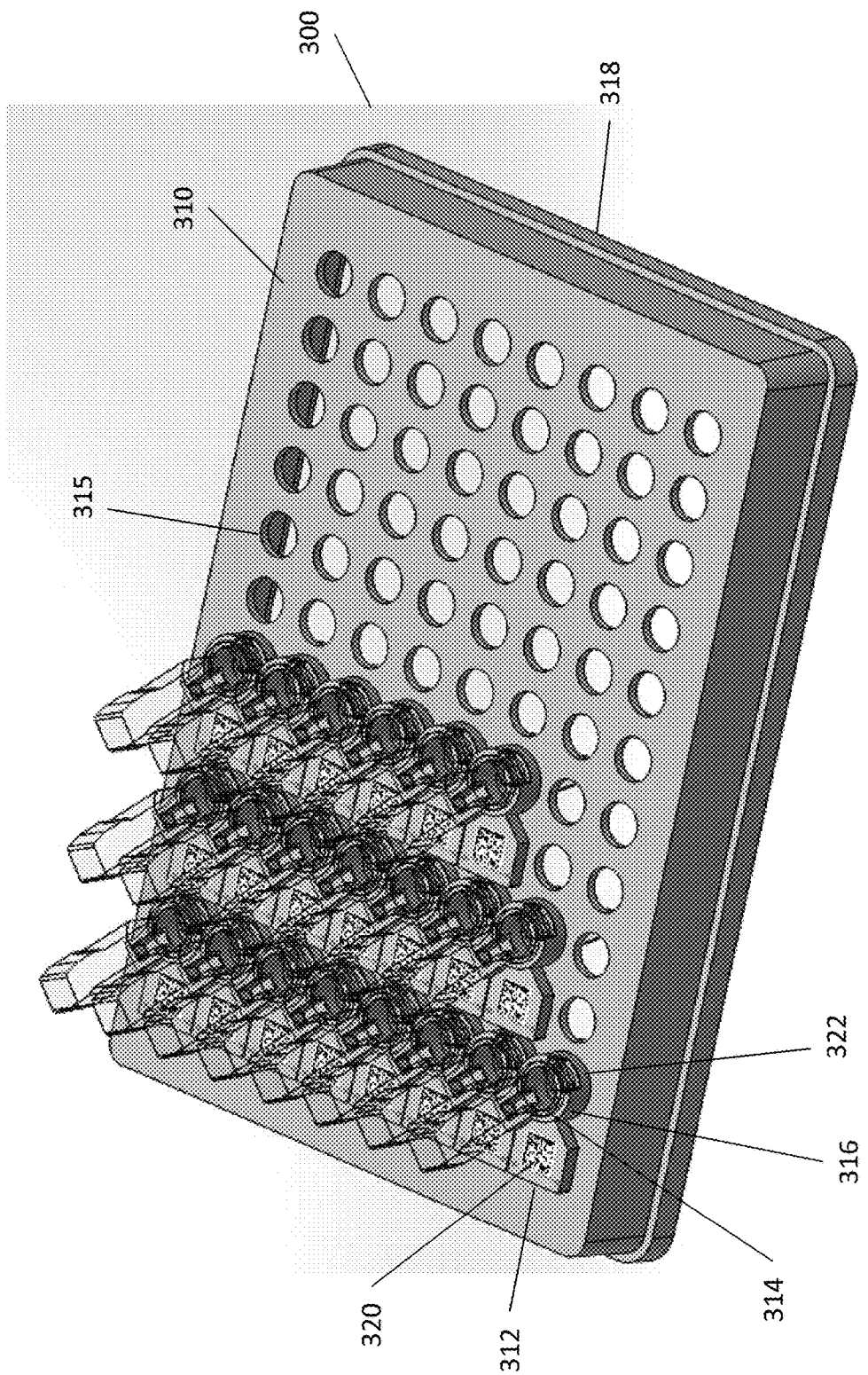
FIGS. 3A-3D depict an embodiment of a system of the present invention.

In preferred systems of the invention, a device is configured to allow positioning within a substrate. This can be accomplished by a protrusion or by the shape of one or more of the components. As shown in FIG. 1, device 100 has a protrusion 158. The protrusion 158 can be configured to snap into or be inserted into an opening within a substrate. FIG. 3A shows a system 300 that comprises a substrate 310 that is able to receive a plurality of devices 312 and vessels 314. Substrate 310 has a skirt 318. Substrate 310 comprises a plurality of openings 315. A device 316 is positioned in the substrate 310 so that the extension member 312 is positioned to allow the protrusion to be inserted into the substrate. The attachment member 322 is configured as a collar where the opening in the collar aligns with an adjacent opening in the substrate. A vessel 314 is positioned in the interior of the collar, such that the vessel also is inserted into the substrate. The extension member 312 displays an identifying mark 320. In this configuration, a particular identification marker is associated with a particular vessel. As positioned, a barcode reader could scan not only one barcode, but all the barcodes displayed by the plurality of devices. In this embodiment, a barcode reader could simultaneously scan a plurality of barcodes and update the computer system or database.

Figure 3B:
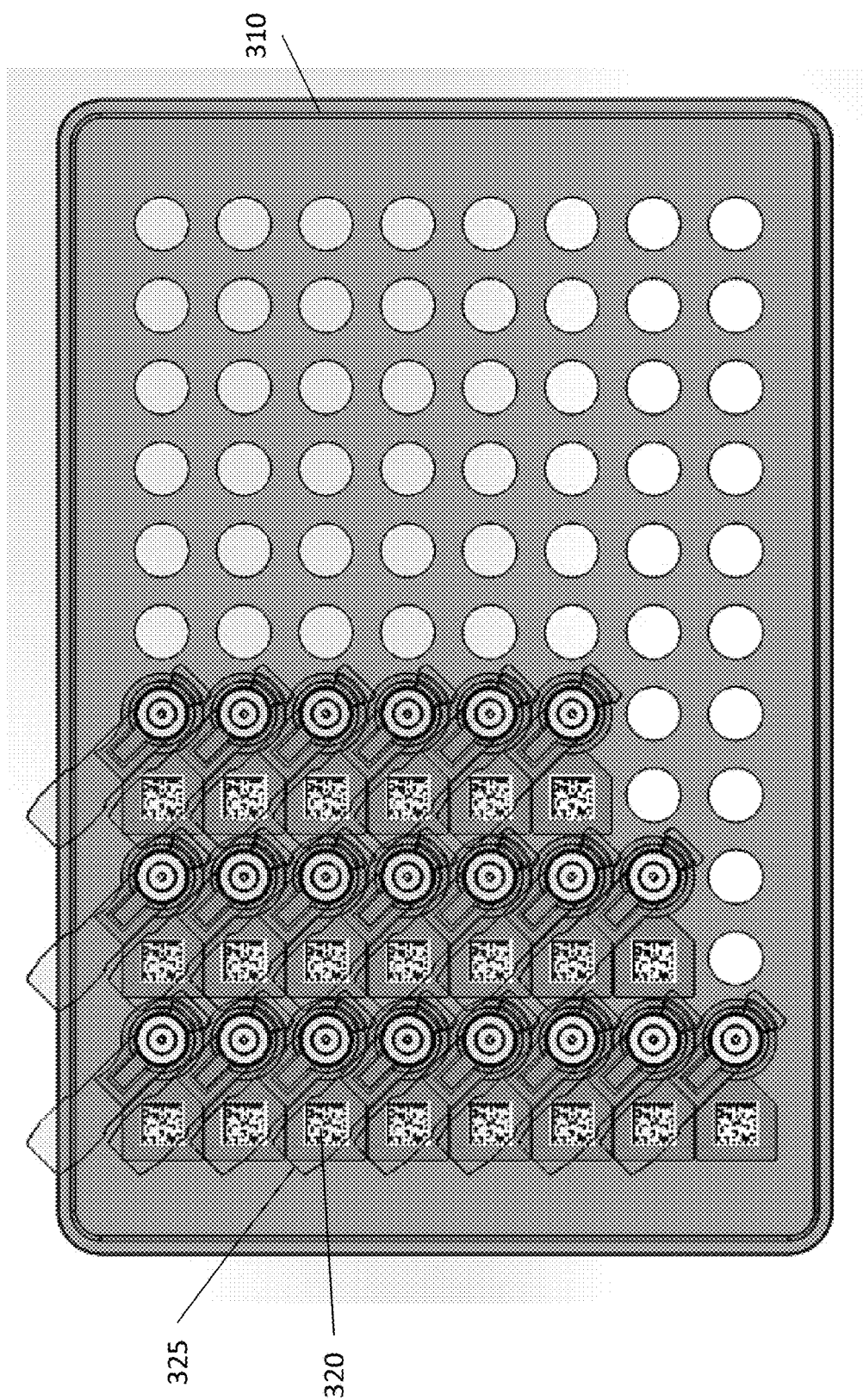

FIG. 3B shows a top view of the embodiment shown in FIG. 3A. As shown in FIG. 3B, the identification markers 320 are arranged so that they are visible from a top or overhead view of the substrate 310. In this configuration, a particular identification marker is associated with a particular vessel. As shown in this view, the identification markers are exposed and could be scanned by a barcode reader. FIG. 3B also depicts that the vessel caps 325 are opened. The recesses in each device are configured so that when the caps are open, the caps do not interfere or overlap with one another. In the embodiments shown in FIGS. 3A and 3B, the device occupies two adjacent openings in the substrate. The protrusion occupies a first opening and the collar aligns with a second opening. It should be appreciated that the collar does not interfere with the second opening in the substrate. Therefore, a vessel is inserted through the collar and into the opening. The vessel nestles into the recesses in collar. In some embodiments, the collar is flush with a flange on the vessel.

Figure 3C:
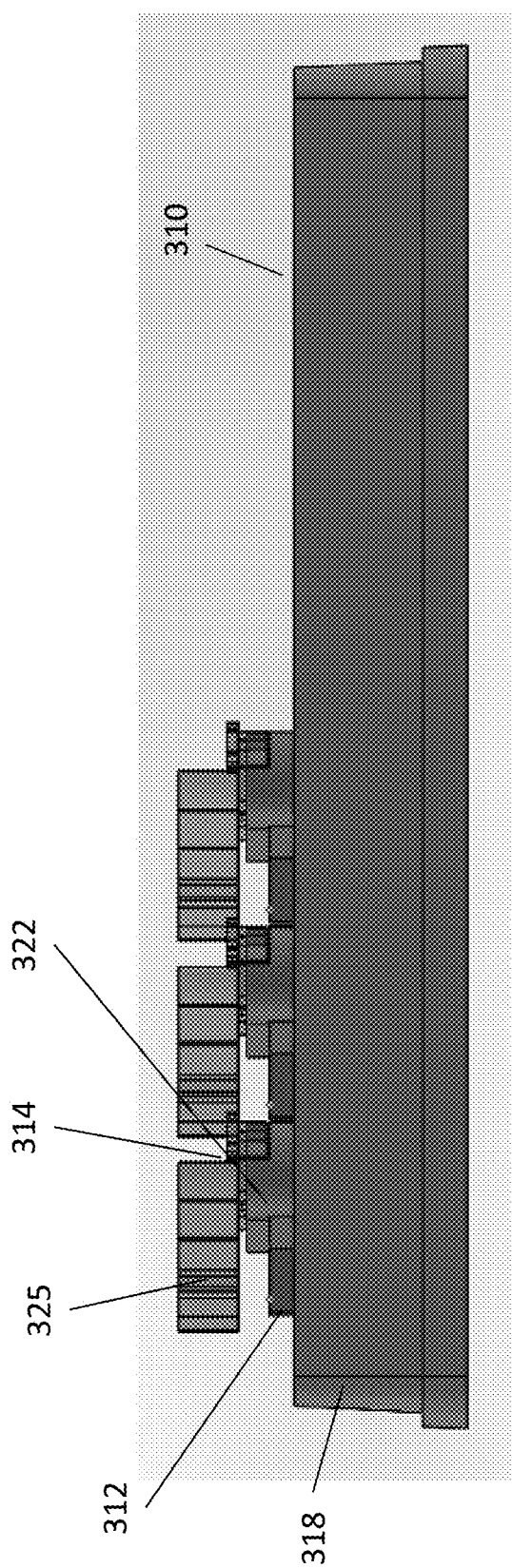
Figure 3D:
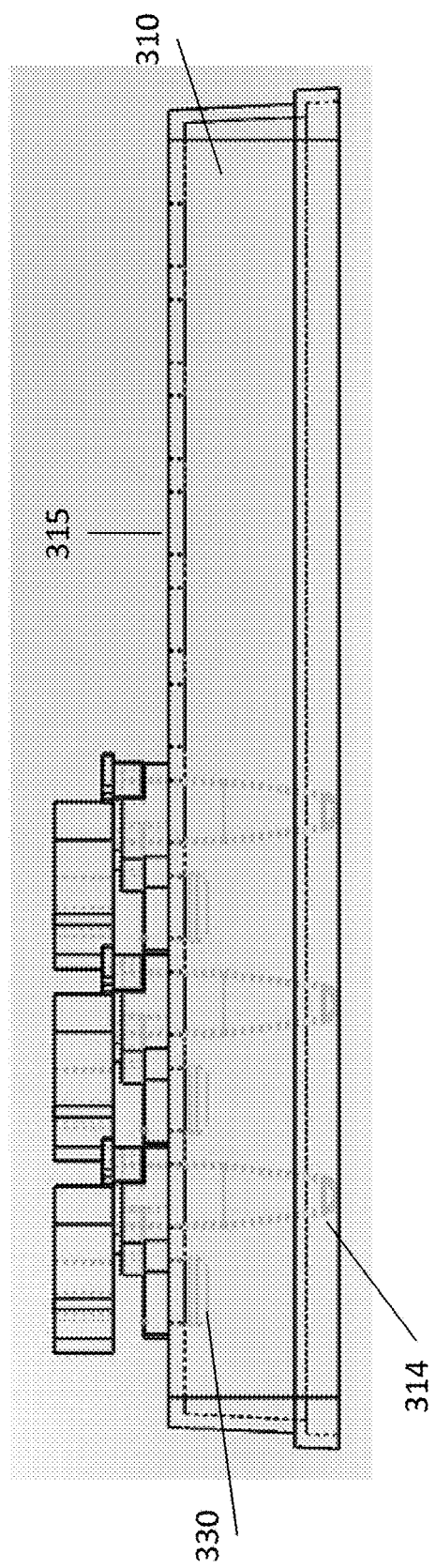

FIG. 3C depicts a side view of the embodiment shown in FIG. 3A and FIG. 3B. In this view, the vessel cap 325 is in the closed positioned. The extension member 312 and attachment member 322 of the device is flush with the substrate surface. The vessel 314 is nestled in the device. As shown in FIG. 3C, the vessel 314 is inserted in the collar and through an opening in the substrate. FIG. 3D depicts a side view of embodiments shown in FIGS. 3A and 3B, however, the vessel 314 and protrusion 330 are shown in phantom.

As shown in FIGS. 3A-3C, the vessel 314 is inserted into the device 316. It should be appreciated that the vessel 314 can be removed from the device 316. Also, the vessel 314 can be removed from the device 316, while the device 316 remains inserted in the substrate 310. Although not shown in FIGS. 3A-3C, the device 316 can be inserted into the substrate 310 without the vessel 314. Also, when the device 316 is inserted in the substrate 310, the vessel can be inserted through the attachment member 322 and into an opening 315 in the substrate 310.

In an aspect of the present invention, the devices including any protrusions can be configured to mate with any substrate whether customized or standardized. FIGS. 3A-3C depict a substrate 310 with openings 315. It should be appreciated that the openings 315 can be indentions or wells. In some embodiments of the invention, a substrate comprises wells, such as a standardized well plate. The device can be configured to mate or fit within the wells of a standardized well plate. In this embodiment, the extension member of the device has a protrusion that fits within a well of a well plate. The attachment member aligns with a well. In some embodiments, the attachment member snaps or fits within the well, where all or part of the well remains uncovered. In this embodiment, a fluid, reagent, etc. could be added to the well. Additionally, a pipette or similar laboratory tool could access the well. In other embodiments, the well is covered by the attachment member. The attachment member could be configured to receive or hold a test tube or vessel above the well plate. In this embodiment, the attachment member would attach or receive the vessel on the lower portion of the vessel.

Figure 4A:
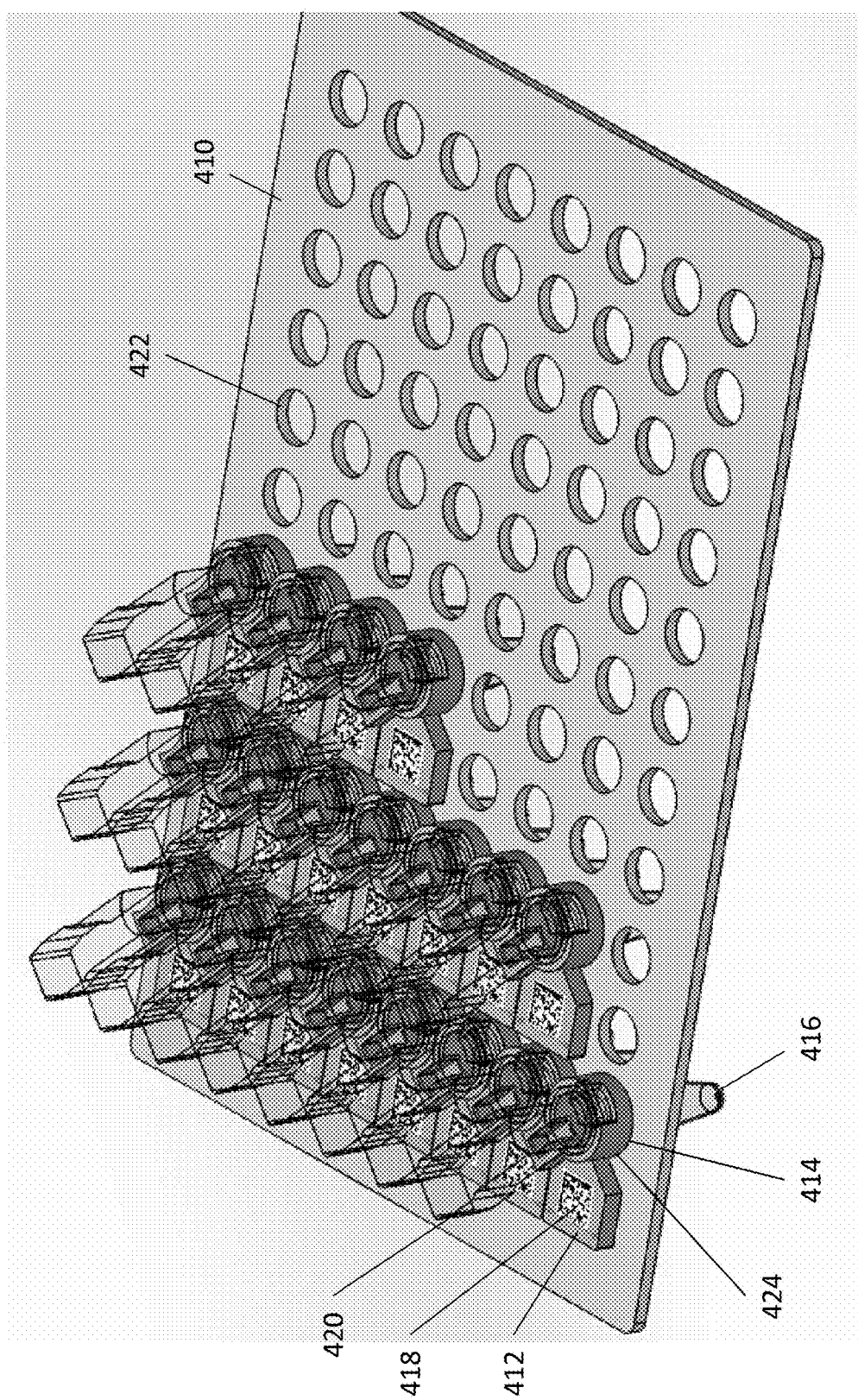
FIGS. 4A-4C depict an embodiment of a system of the present invention.

FIG. 4A depicts a similar embodiment to the embodiment shown in FIG. 3A, however, in FIG. 4A, the substrate lacks a support or skirt. The substrate 410 comprises a plurality of openings 422. The device 424 comprises an extension member 412 and an attachment member 414. The attachment member is shown in FIG. 4A as a collar that aligns with an opening 422. A protrusion (not shown) on the bottom surface of the extension member inserts into an adjacent opening. A vessel 416 fits within the attachment member 414 and opening in the substrate 410. As shown in FIG. 4A, the vessel cap 420 is in the open position. The recesses in the attachment member are configured to allow the vessel cap 420 to move from an opening position to a closed position without interfering with proximate vessels. The extension member 412 displays an identification marker 418. In this configuration, a particular identification marker is associated with a particular vessel.

Figure 4B:
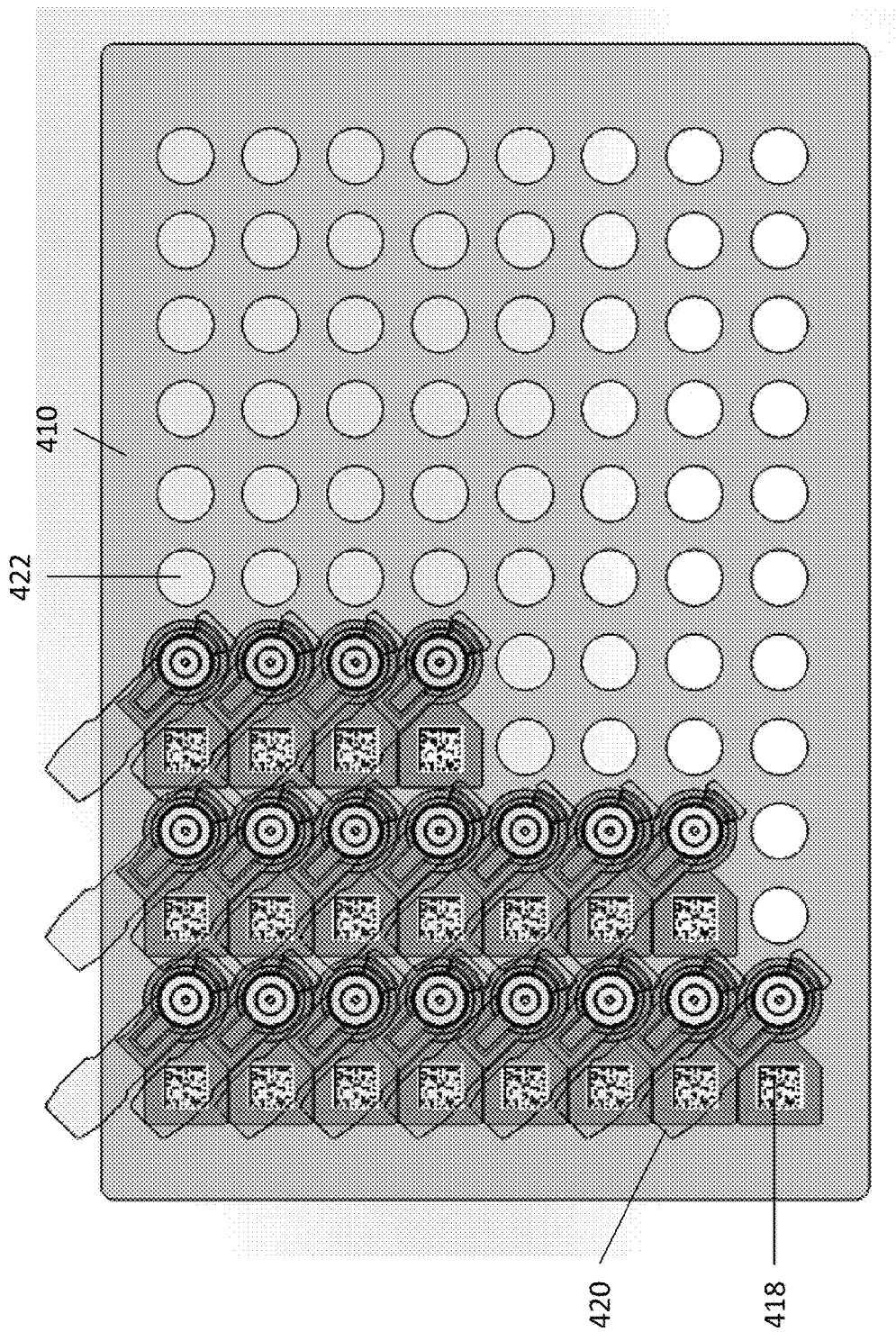

FIG. 4B depicts a top or overhead view of the embodiment shown in FIG. 4A. The substrate 410 comprises a plurality of openings 422. The vessel caps 420 are shown in the open position. It should be appreciated that the vessel caps 420 can be moved to the closed position without interference from the device. The identification markers 418 are displayed. It should be appreciated that the identification markers are presented to allow a barcode reader to scan the displayed barcodes. In some embodiments, the barcodes are scanned serially. In other embodiments, the barcodes are scanned simultaneously.

Figure 4C:
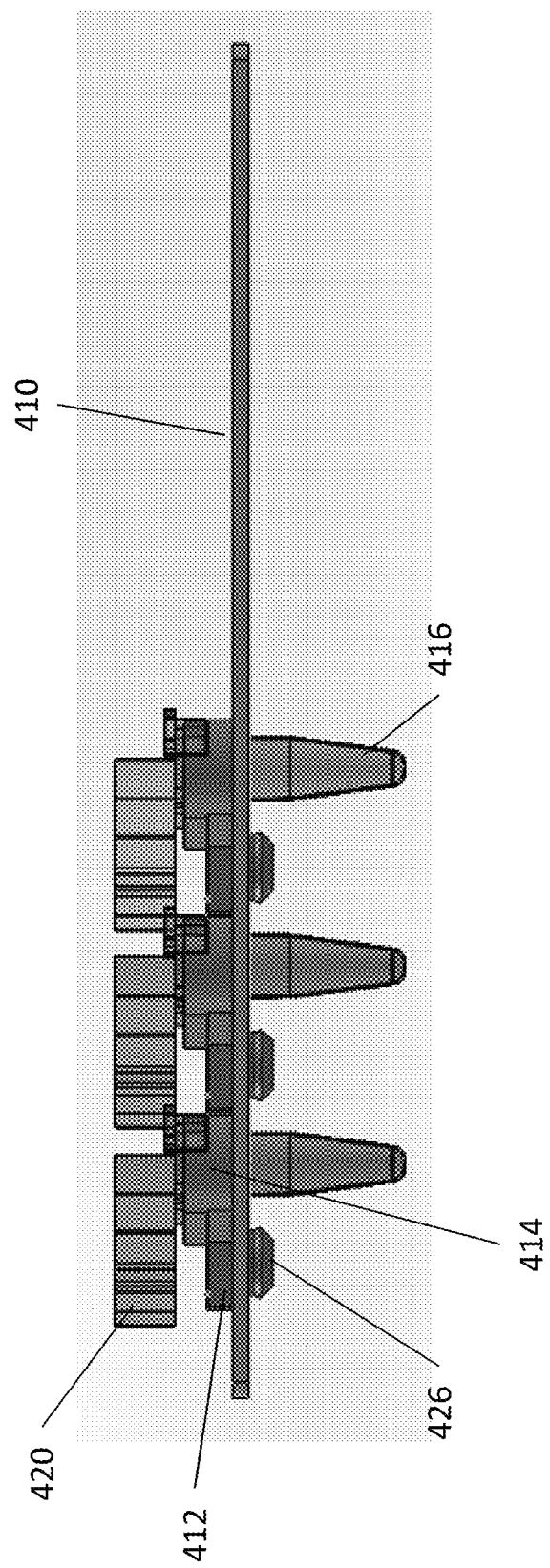

FIG. 4C depicts a side view of the embodiment shown in FIGS. 4A and 4B. From this viewpoint, the vessels 416 are shown nestled in the attachment member 414 and through an opening in the substrate 410. The extension member 412 comprises a protrusion 426 that is inserted into an opening in the substrate 410. In this view, the vessel caps 420 are shown in the closed position.

Figure 5:
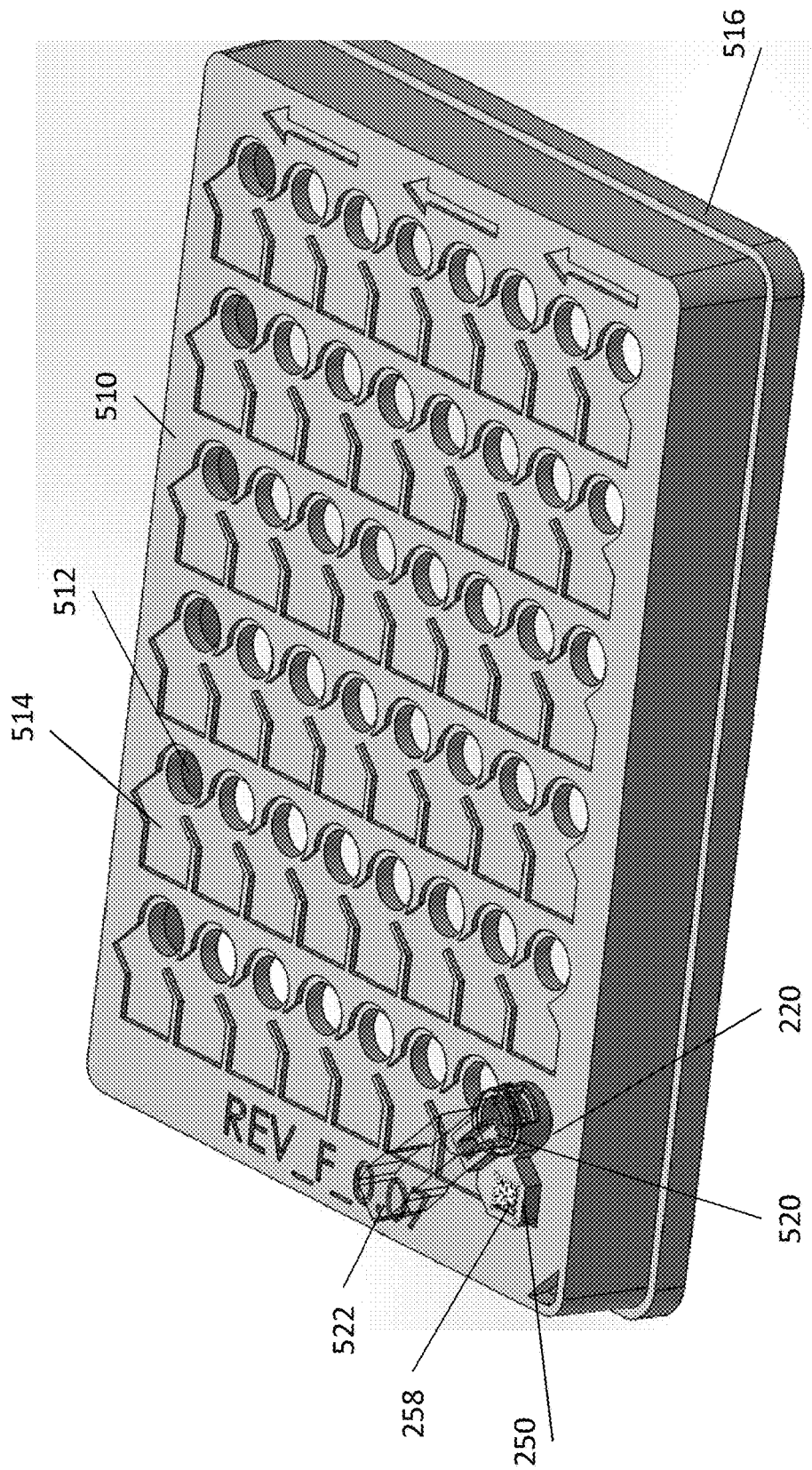
FIG. 5 depicts an embodiment of a system of the present invention.

As discussed above, the devices can be manufactured into any shape. In aspects of the invention, a component of the device fits within a recess in a substrate. FIG. 5 depicts an embodiment where a substrate 510 comprises a plurality of openings 512 and recesses 514. As depicted in FIG. 5, a recess 514 is associated with an opening 512. The substrate 510 also comprises a skirt 516. As shown in FIG. 2, a device 200 comprises an attachment member 220 and an extension member 250. The extension member 250 has a top portion 252 bottom portion 254. The top portion 252 is configured to display an identification marker 258. The extension member 250 is configured to fit within a recess 514. As shown in FIG. 5, the extension member 250 fits within recess 514. The attachment member 220 is configured to align with an opening 512. In this embodiment, a vessel 520 nestles within the attachment member 220 and through an opening 512. In this configuration, a particular identification marker is associated with a particular vessel. Although the vessel cap 522 is shown in the open position, the vessel cap 522 can be moved to the closed position without interference from the device. It should be appreciated that the openings 512 could be indentions or wells.

Figure 6A:
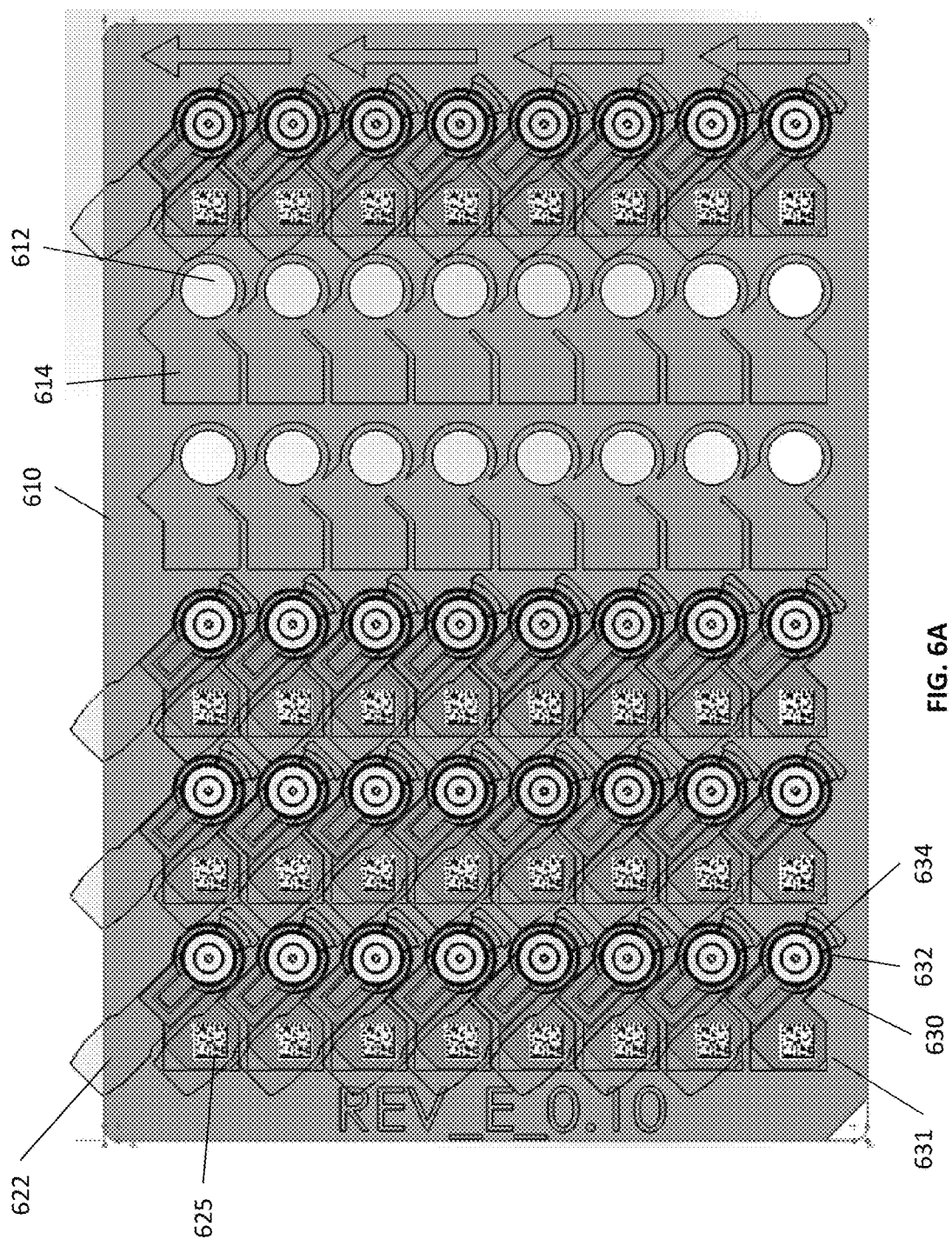
FIGS. 6A-6B depict an embodiment of a system of the present invention.

FIG. 6A depicts another embodiment of the invention where a substrate 610 comprises a plurality of recesses 614 and openings 612. It should be appreciated that the openings 612 can also be indentions or wells. In this embodiment, devices 630 of the invention are inserted into the substrate 610. The extension member 631 of the device 630 is configured to fit within a recess 614. The attachment member 632 of the device 630 is configured to align with an opening 612 in the substrate 610 such that a vessel 634 is nestled in the attachment member 632 and through the opening 612. The extension member 631 displays an identification marker 625. In this configuration, each vessel is associated with a particular identification marker. It should be appreciated that the identification markers are displayed to allow a barcode reader to scan the identification markers. The barcode may scan the identification markers serially, or simultaneously.

Figure 6B:
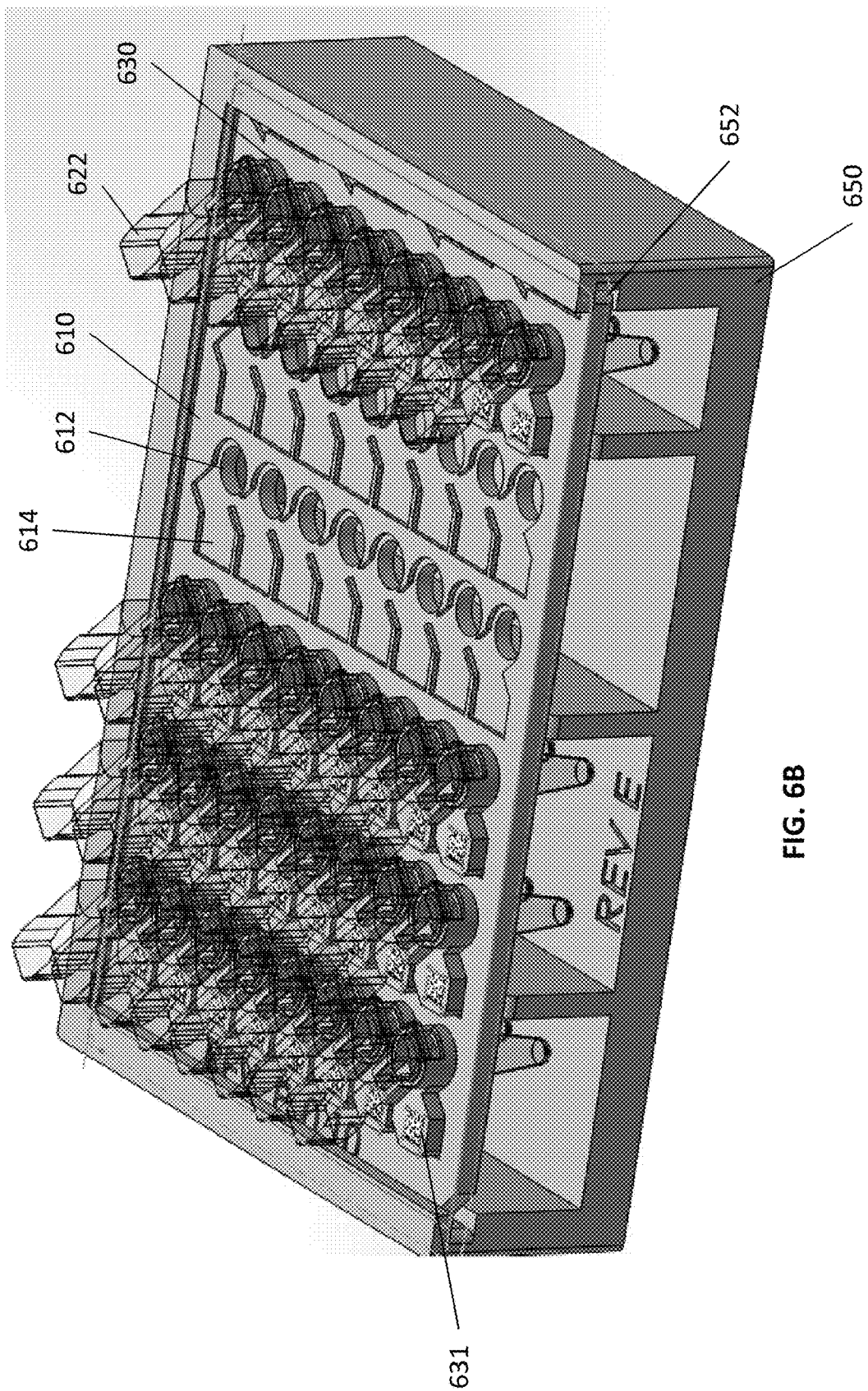

FIG. 6B depicts the substrate 610 inserted in a platform 650. Substrate 610 slides into platform 650 via slots, or grooves 652 formed within platform 650. Platform 650 positions substrate 610 in a substantially horizontal position, while displaying identification markers 631. In this orientation, the identification markers 631 are displayed so that a barcode reader could scan the identification markers.

As described herein, the device can be separate from the vessel and attachable to the vessel. Alternatively, the vessel and the device can be formed integrally as a single unit. In other words, an attachment member is not needed because the vessel and the extension member are melded into a single form; similar to a vessel with a protrusion. This protrusion can be configured to accommodate and display an identifying mark.

In other embodiments, the devices of the invention are configured to not only be attachable to a vessel, but also attachable to each other. In this embodiment, two devices join together, or are releasably coupled. When two devices are joined and each device is attached to a vessel, the two devices hold and position the vessels. In some embodiments, multiple devices are joined together without the need of a supporting substrate. In some embodiments, the devices are configured so that when joined and attached to vessels, the vessels are configured into an array. The array can be a single row of vessels or a matrix of vessels. The matrix can have any dimension. For example, the array could be 8 vessels by 12 vessels. In some embodiments, the array could be configured to match the dimensions of a standardized well plate, such as standardized 96 well plate.

As discussed above, the devices of the present invention generally comprise an attachment member and an extension member. The attachment member is joined to the extension member. The attachment member attaches to or receives a sample vessel. In some embodiments, the extension member comprises a feature, where the feature allows for two devices to be joined together. Additionally, in some embodiments, the extension member also accommodates an identifying mark. It should be appreciated that any type of releasable fastener can be used with the present invention. For example, in some embodiments, the extension member comprises grooved slots, such as a T-slot. A second extension member comprises complimentary slots such that the grooves of the first extension member mate or are received into the slots of a second extension member, thereby joining the two extension members.

In other embodiments of the invention, the extension members are joined by one or more snap joints. Snap joints are known in the art and usually comprise a protruding part of one component, e.g. a hook, stud or bead, that is deflected briefly during the joining operation and catches in a depression or undercut in the mating component. The force necessary to separate the components varies on the design of the snap joint. Examples of snap joints include cantilever snap joints, u-shaped snap joints, torsion snap joints, and annular snap joints. In some embodiments, one extension member has a male feature and another extension member has a female feature, such that the male and female features are mated, they join the two extension members.

It should be appreciated that the features for joining two devices together can be located on any surface of the device. For example, the attachment member can comprise such a feature. This feature could be located on any surface area of the attachment member. In other embodiments, the extension member can comprise the feature. Further, the feature could be located on a top portion, bottom portion, or side portion of the extension member. In an aspect of the invention, the device allows for individual wells and vials to be integrated into an automated laboratory. LIMS and robotic laboratories allow for sample tracking, high performance computing and analysis, and data handling in high-throughput biotechnology research and industrial laboratories. Clinical and high-throughput laboratories shorten sample turnaround time and reduce the possibility of error. Automation dramatically improves performance. An automated, robotic, and LIMS based laboratory is able to inform liquid-handling robotics on sample placement location and container type; track and record any information reported by robotics; assign samples to workflows; pool samples; add reagent labels to samples, and assign next steps in the workflow. Instruments within an automated laboratory may include automated liquid handling instruments (e.g.

pipetting systems, dispensers, microplate washers, automated workstations (multi-purpose), decappers/recappers etc.); microplate readers; and stand-alone robots (e.g. robotic arms, track robot systems, etc.). An automated laboratory may also include software and informatics, such as workstation/unit automation software, Lab Information Management Systems (LIMS), Electronic Lab notebook (ELN), and Scientific Data Management System (SDMS). Other components include automated storage and retrieval systems, barcode readers, weighing platforms, sealers, etc. Automated laboratories have applications in clinical diagnostics (pre-analytics/sample preparation, ELISA, sample distribution, splitting and archiving); drug discovery (high throughput screening, next generation sequencing (NGS) sample preparation, ADME screening, compound weighing and dissolution); genomics solutions (genotyping, PCR applications, DNA/RNA quantification and normalization); and proteomics solutions (protein purification and crystallography, MALDI plate spotting).

Using an automated laboratory system, the barcode on the device can be scanned into a computer system. Once scanned, the barcode is entered into the computer system or database. A user is able to track or locate the vessel once the barcoded vessel is incorporated into the automated laboratory system. A user could also determine samples, reagents, and instruments associated with the vessel during the laboratory process. As reagents or samples are added to the vessel, via the barcode, computer system can be updated with this information. As the vessel is transported from one instrument to another, scanning the barcode allows for tracking the vessel throughout the laboratory.

Figure 7:
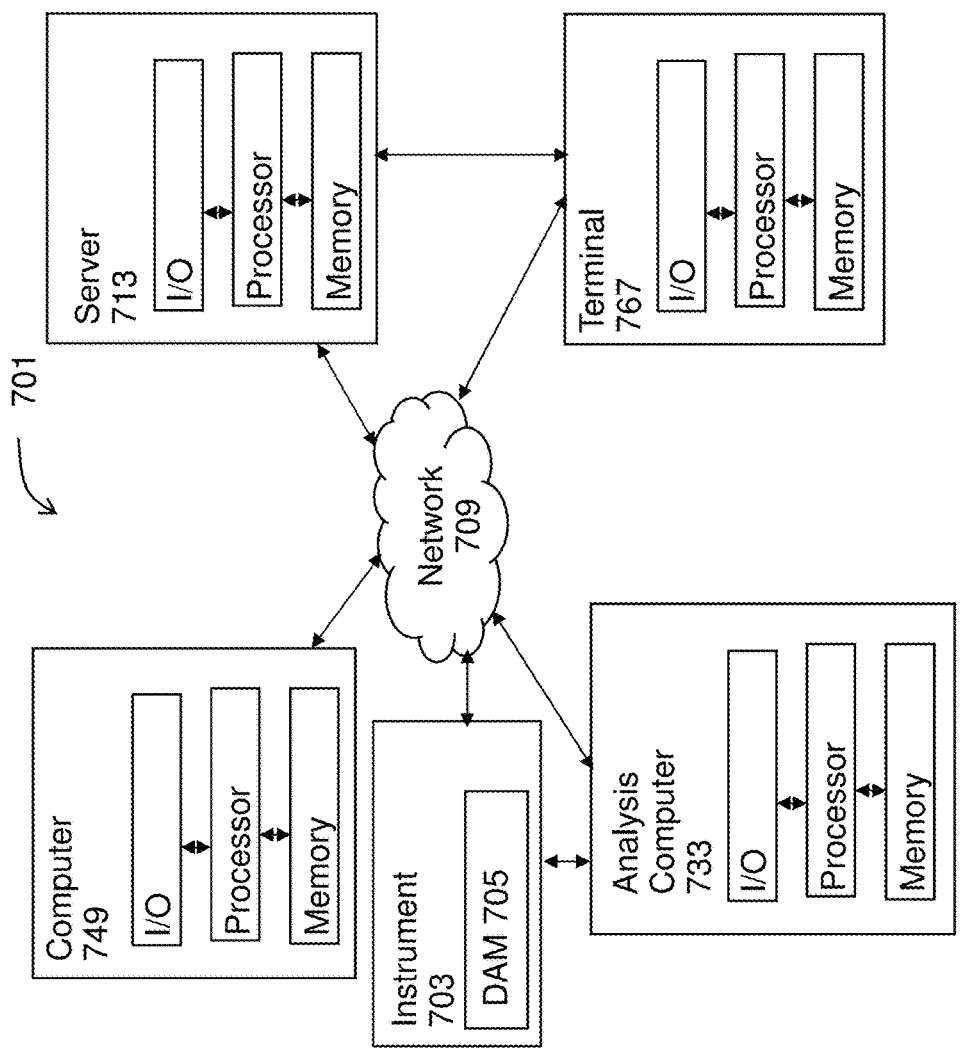
FIG. 7 depicts a diagram of a system of the invention.

FIG. 7 depicts a diagram of a system 701 according to embodiments of the invention. System 701 may include an analysis instrument 703. Instrument 703 includes a barcode reader that scans barcodes, or other identifying marks during laboratory processes. Instrument 703 includes a data acquisition module 705 to obtain barcode data. Instrument 703 may optionally include or be operably coupled to its own, e.g., dedicated, analysis computer 733 (including an input/output member, one or more processor, and memory). Additionally or alternatively, instrument 703 may be operably coupled to a server 713 or computer 749 (e.g., laptop, desktop, or tablet) via a network 709.

Computer 749 includes one or more processors and memory as well as an input/output member. Where methods of the invention employ a client/server architecture, steps of methods of the invention may be performed using the server 713, which includes one or more of processors and memory, capable of obtaining data, instructions, etc., or providing results via an interface module or providing results as a file. The server 713 may be engaged over the network 709 by the computer 749 or the terminal 767, or the server 713 may be directly connected to the terminal 767, which can include one or more processors and memory, as well as an input/output member.

In system 701, each computer preferably includes at least one processor coupled to a memory and at least one input/output (I/O) member. A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Preferably, each computer includes a non-transitory memory such as a solid state drive, flash drive, disk drive, hard drive, etc. While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Any of the software can be physically located at various positions, including being distributed such that portions of the functions are implemented at different physical locations.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed:

1. A device for identifying a vessel, the device comprising:
    a body having an attachment member and an extension member, wherein the attachment member is configured to contact a portion of a vessel and the extension member is configured to display an identifying mark comprising a barcode adjacent to an opening in the vessel.
2. The device of claim 1, wherein the attachment member is a collar that fits on a shaft of the vessel.
3. The device of claim 2, wherein the collar is held to the vessel by frictional forces.

4. The device of claim 1, wherein the attachment member comprises a recess and the recess is configured to receive a portion of the vessel.

5. The device of claim 4, wherein the recess is configured to receive a portion of the vessel and prevents the vessel from rotating.

6. The device of claim 1, wherein the device is removable from the vessel.

7. The device of claim 1, wherein the extension member comprises a top portion and a bottom portion.

8. The device of claim 7, wherein the top portion of the extension member is configured to receive an identifying mark.

9. The device of claim 7, wherein the bottom portion of the extension member is configured to receive an identifying mark.

10. The device of claim 7, wherein the bottom portion of the extension member comprises a protrusion.

11. The device of claim 10, wherein the protrusion is configured to fit with a well in a well plate.

12. The device of claim 1, wherein the extension member is configured to couple with a recess in a substrate.

13. The device of claim 1, wherein the vessel is a test tube or vial.

14. The device of claim 1, wherein the barcode is a two-dimensional barcode.

15. A vessel comprising:
a generally cylindrical body with a closed bottom so as to form a receptacle for receiving a sample; and
a protrusion extending from the body of the vessel, wherein the protrusion is configured to accommodate an identifying mark comprising a barcode.

16. The vessel of claim 15, wherein the barcode is a two-dimensional barcode.

17. The vessel of claim 15, wherein the identifying mark is an alpha or numerical character.

18. The vessel of claim 15, wherein the vessel comprises a top portion and a bottom portion.

19. The vessel of claim 18, further comprising a cap attached to the top portion of the vessel by a hinge.

20. A system for holding a plurality of identified vessels, the system comprising:
a substrate comprising at least one recess and at least one opening configured to receive a vessel; and
a device for identifying a vessel, the device comprising: a body having an attachment member and an extension member, wherein the attachment member is configured to contact a portion of a vessel and the extension member is configured to display an identifying mark comprising a barcode adjacent to an opening in the vessel.

21. The system of claim 20, wherein the attachment member is a collar that fits on a shaft of the vessel.

22. The system of claim 21, wherein the collar is held to the vessel by frictional forces.

23. The system of claim 20, wherein the attachment member comprises a recess and the recess is configured to receive a portion of the vessel.

24. The system of claim 23, wherein the recess is configured to receive a portion of the vessel and prevent the vessel from rotating.

25. The system of claim 20, wherein the extension member comprises a top portion and a bottom portion.

26. The system of claim 25, wherein the top portion of the extension member is configured to receive an identifying mark.

27. The system of claim 25, wherein the bottom portion of the extension member is configured to receive an identifying mark.

28. The system of claim 20, wherein the vessel is a test tube or vial.

29. The system of claim 20, wherein the barcode is a two-dimensional barcode.

30. The system of claim 20, wherein the identifying mark is an alpha or numerical character.

31. The system of claim 20, wherein the extension member orients the identifying mark to be scanned by a barcode scanner.

32. The system of claim 31, wherein the barcode scanner scans the plurality of identified vessels simultaneously.

33. A system for assembling a plurality of vessels, the system comprising:
a first device comprising a body having an attachment member and an extension member, wherein the attachment member is configured to contact a portion of a vessel and the extension member comprises a feature; and
a second device comprising a body having an attachment member and an extension member, wherein the attachment member is configured to contact a portion of a vessel and the extension member comprises a complimentary feature, wherein the feature and the complimentary feature join the first and second devices;
wherein the extension members of the first and second devices are configured to display an identifying mark comprising a barcode adjacent to an opening in the vessel.

34. The system of claim 33, wherein the feature is a first slot and the complimentary feature is a second slot, wherein the second slot slides into the first slot to join the devices.

35. The system of claim 33, wherein the feature is cantilever and the complimentary feature is a depression where the cantilever is snapped into the depression, thereby joining the devices.

36. The system of claim 33, where in the feature is male feature and the complimentary feature is a female feature, wherein the female feature is received into the male feature to join the two devices together.

37. The system of claim 33, wherein the barcode is a two-dimensional barcode.

38. The system of claim 33, wherein the identifying mark is an alpha or numerical character.

39. The system of claim 33, wherein the extension member orients the identifying mark to be scanned by a barcode scanner.

40. The system of claim 39, wherein the barcode scanner scans a plurality of identifying marks simultaneously.

41. The system of claim 33, further comprising a plurality of first devices and second devices joined together to form an array.

42. The system of claim 41 wherein the array is configured into the dimensions of a standardized well plate.

43. The system of claim 33, where the identifying mark is colored.

* * * * *